United States Patent [19]

Giannessi et al.

[11] Patent Number: 5,532,410
[45] Date of Patent: Jul. 2, 1996

[54] PROCESS FOR MANUFACTURING L(-)-CARNITINE FROM A WASTE PRODUCT HAVING OPPOSITE CONFIGURATION

[75] Inventors: Fabio Giannessi, Rome; Nazareno Scafetta, Pavona di Albano; Ida Bernabei, Nettuno; Maria O. Tinti; Francesco De Angelis, both of Rome, all of Italy

[73] Assignee: Sigma-Tau Industrie Farmaceutiche Ruinite S.p.A., Rome, Italy

[21] Appl. No.: 224,513

[22] Filed: Apr. 4, 1994

[30] Foreign Application Priority Data

Apr. 8, 1993 [IT] Italy .................. 93A000227

[51] Int. Cl.$^6$ ................................ C07C 229/00
[52] U.S. Cl. ............................ 562/567; 558/48
[58] Field of Search .......................... 562/567

[56] References Cited

U.S. PATENT DOCUMENTS 3,096,368  7/1963  Binon .................................. 562/567
4,413,142  11/1983  Fiorini ................................. 562/567

*Primary Examiner*—Michael L. Shippen
*Attorney, Agent, or Firm*—Oblon, Spivak, McClelland, Maier & Neustadt

[57] ABSTRACT

L-(−)-carnitine is prepared from D-(+)-carnitinamide by (a) reacting D-(+)-carnitinamide in an acid medium with a straight or branched chain aliphatic alcohol thereby forming D-(+)-carnitine ester, (b) acylating the D-(+)-carnitine ester with an anhydride $R_2O$, thereby forming an acylated ester intermediate, (c) acid hydrolyzing the ester group of the acyl carnitine ester thereby obtaining acyl D-(+)-carnitine, (d) lactonizing the acyl D-(+)-carnitine to a lactone of L-(−)-carnitine, and (e) reacting the lactone with base thereby forming L-(−)-carnitine.

6 Claims, No Drawings

PROCESS FOR MANUFACTURING L(-)-CARNITINE FROM A WASTE PRODUCT HAVING OPPOSITE CONFIGURATION

BACKGROUND OF THE INVENTION

1. Field of the Invention

The present invention relates to an improved process for manufacturing L-(−)-carnitine from a starting compound containing an asymmetrical carbon atom having a configuration opposite to that of L-(−)-carnitine. The process of the present invention overcomes the drawbacks of conventional processes which first convert a starting compound into an achiral intermediate, generally crotonobetaine or gamma-butyrobetaine, and then convert the achiral intermediate to L-(−)-carnitine. The process of the present invention uses D-(+)-carnitinamide as starting compound.

2. Discussion of the Background

Carnitine contains a single center of asymmetry and therefore exists as two enantiomers, designated D-(+)-carnitine and L-(−)-carnitine. Of these, only L-(−)-carnitine is found in living organisms, where it functions as a vehicle for transporting fatty acids across mitochondrial membranes. Whilst L-(−)-carnitine is the physiologically-active enantiomer, racemic D,L-carnitine has conventionally been used as a therapeutic agent. It is now recognized, however, that D-(+)-carnitine is a competitive inhibitor of carnitine acyltransferases, and that it diminishes the level of L-(−)-carnitine in myocardium and skeletal muscle.

It is therefore essential that only L-(−)-carnitine be administered to patients undergoing haemodialysis treatment or treatment for cardiac or lipid metabolism disorders. The same requirement applies to the therapeutic utilization of acyl derivatives of carnitine for treating disorders of the cerebral metabolism, peripheral neuropathies, peripheral vascular diseases and the like. These disorders are typically treated with acetyl L-(−)-carnitine and propionyl L-(−)-carnitine, which are obtained by acylating L-(−)-carnitine.

Various chemical procedures have been proposed for the industrial-scale production of carnitine. Unfortunately, these procedures are not stereospecific and produce racemic mixtures of D-(+)- and L-(−)-isomers. It is thus necessary to apply resolution methods in order to separate the enantiomeric constituents of the racemate.

Typically, the D,L-racemic mixture is reacted with an optically active acid (e.g. D-(−)-tartaric acid, D-(+)-camphorsulfonic acid, (+)-dibenzoyl-D-(−)-tartaric acid, N-acetyl-L-(+)-glutamic acid and D-(+)-camphoric acid) to obtain two diastereoisomers which can be separated from each other. In the classic process disclosed in U.S. Pat. No. 4,254,053, D-(+)-camphoric acid is used as the resolution agent of a racemic mixture of D,L-carnitinamide, obtaining D-(+)-carnitinamide as a by-product, and L-(−)-carnitinamide which, by hydrolysis, gives L-(−)-carnitine.

However, these resolution procedures are complex and costly, and in all cases result in the production of equimolar quantities of L-(−)-carnitine and D-(+)-carnitine or a precursor thereof as by-product, having configuration opposite to that of L-(−)-carnitine. Several microbiological processes have recently been proposed for producing L-(−)-carnitine via stereospecific transformation of achiral derivatives obtained from the huge amounts of D-(+)-carnitine (or of a precursor thereof, such as D-(+)-carnitinamide) which are generated as by-products in the industrial production of L-(−)-carnitine.

These processes are generally predicated upon the stereospecific hydration of crotonobetaine to L-(−)-carnitine, and differ principally by virtue of the particular microorganism employed to accomplish the biotransformation of interest. See, for example, the processes disclosed in: EP 0 2 1444 (HAMARI), EP 0 122 794 (AJINOMOTO), EP 0 148 132 (SIGMA-TAU), JP 275689/87 (BIORU), JP 61067494 (SEITETSU), JP 61234794 (SEITETSU), JP 61234788 (SEITETSU), JP 61271996 (SEITETSU), JP 61271995 (SEITETSU), EP 0 410 430 (LONZA), EP 0 195 944 (LONZA), EP 0 158 194 (LONZA), and EP 0 457 735 (SIGMA-TAU).

On the other hand, JP 62044189 (SEITETSU) discloses a process for stereoselectively producing L-(−)-carnitine starting from gamma-butyrobetaine, which is in turn obtained enzymatically from crotonobetaine.

All of these processes have several drawbacks. First, D-(+)-carnitine must first be converted to an achiral compound (crotonobetaine, gamma-butyrobetaine) before it can be used as the-starting compound in all of the aforesaid microbiological processes.

In addition, the microbiological procedures proposed to date have not proven practicable for manufacturing L-(−)-carnitine on an industrial scale for one or more of the following reasons:

(i) the yield of L-(−)-carnitine is extremely low;

(ii) the microorganisms must be cultivated in a costly nutritive medium; (iii) the microorganism can only tolerate low concentrations [up to 2–3% (w/v)] of crotonobetaine;

(iv) side reactions occur, such as the reduction of crotonobetaine to gamma-butyrobetaine or the oxidation of L-(−)-carnitine to 3-dehydrocarnitine.

These side reactions reduce the final yield of L-(−)-carnitine.

In order to overcome all of the aforesaid drawbacks of the known processes, in the Italian patent application RM 92 A 000 915 filed on Dec.21, 1992 in the name of the same applicants as the present application, not available to public inspection at the filing date of this application, a process has been disclosed which allows high yields of L-(−)-carnitine to be obtained starting from a by-product having configuration opposite to that of L-(−)-carnitine (such as D-(+)-carnitinamide) with no need to first convert the starting by-product into an achiral intermediate.

This process which is illustrated in the following reaction scheme 1:

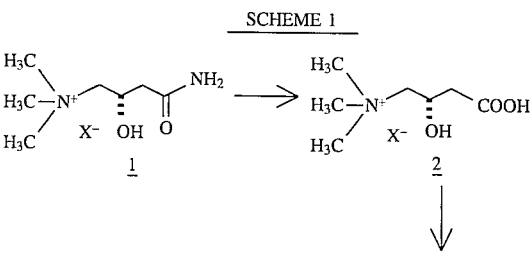

5,532,410

SCHEME 1 -continued

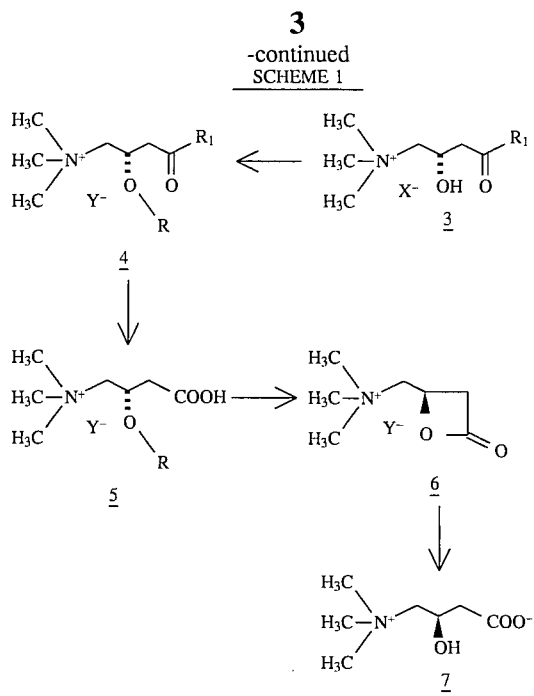

comprises hydrolyzing a D-(+)-carnitinamide salt 1 to D-(+)-carnitine 2 and esterifying 2 into ester 3 (via known methods) wherein R1 is preferably arylalkoxy, e.g. benzyloxy.

The ester 3 is then converted to the acyl derivative 4 wherein Y, which can be the same as X, is preferably a counterion, e.g. perchlorate, imparting solubility to 4. OR is a leaving group wherein R is preferably an alkylsulfonyl group having 1–12 carbon atoms, e.g. mesyl.

The acylation of 3 to 4 is carried out preferably in pyridine by reacting the ester 3 with an acylating agent RY wherein Y is halogen and R is an acyl group as defined above. Preferably RY is the chloride of the selected acyl group.

The ester group —$COR_1$ of 4 ($R_1$=benzyloxy) is hydrogenated to carboxyl group thus giving acyl D-(+)-carnitine 5 which is converted to the lactone 6 of L-(−)-carnitine. The lactonization is suitably carried out in an aqueous basic environment: either with $NaHCO_3$(ratio 1:1) or with an AMBERLITE IRA-402 basic resin activated in $HCO_3^-$ form or with an LA2 resin. The lactone is isolated by evaporating the aqueous solution or precipitating it as a salt (for example, as tetraphenylborate or reineckate).

Finally, lactone 6 is suitably converted to L-(−)-carnitine inner salt 7. The lactone is dissolved in water and the resulting solution treated with a base such as $NaHCO_3$(ratio 1:1), for 8–24 hours.

L-(−)-carnitine can suitably be purified from the salts which are formed from the X anion, from the excess, if any, of the acyl halogenide, from pyridine, and the like, by chromatographing the aqueous solution on a strongly acidic resin such as IR 120, eluting with water and then with $NH_4OH$, or alternatively eluting first on a strongly basic resin such as AMBERLITE IRA 402 activated in OH form and thereafter on a weakly acid resin such as AMBERLITE IRC-50.

The process of the present invention which is illustrated in the following reaction scheme 2 constitutes a remarkable improvement over the previous process.

SCHEME 2

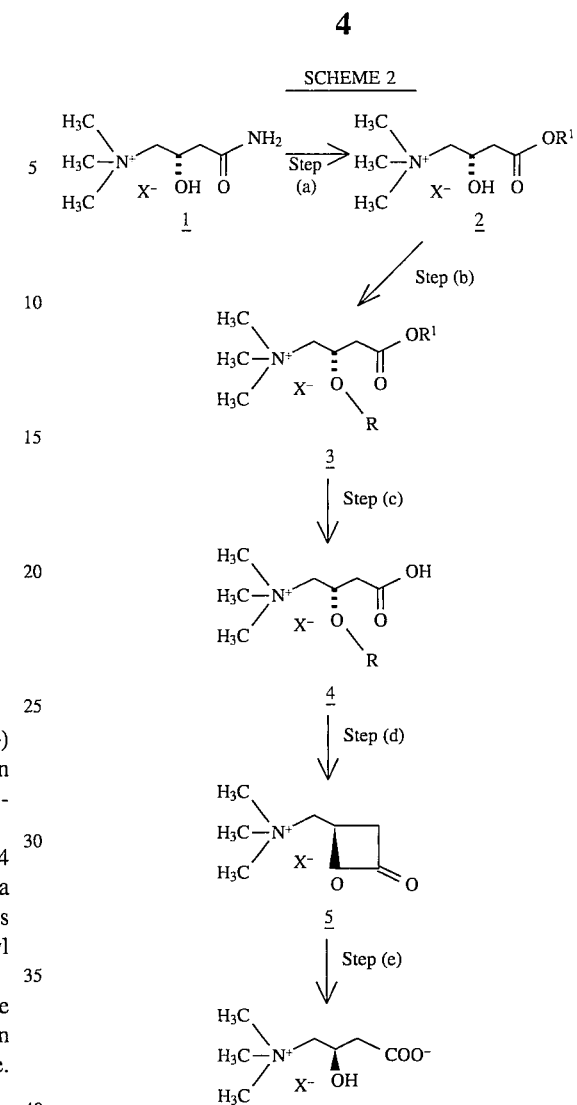

Indeed:
(1) D-(+)-carnitinamide 1 is directly converted to ester 2 (without previous conversion to D-(+)-carnitine);
(2) acylation (particularly, mesylation) of 2 to 3 can be carried out in the absence of solvents, particularly pyridine the use of which brings about serious drawbacks;
(3) the ester group of acyl derivatives 3 is converted into the carboxyl group of acyl derivative 4 via simple acid hydrolysis, thus avoiding the drawbacks of hydrogenation reduction, which are particularly serious when the process is conducted on an industrial scale.

In detail, with reference to the reaction scheme 2, D-(+)-carnitinamide 1 is converted into ester 2 via conventional procedures, in the presence of an excess of alcohol, preferably an alkanol having 1–4 carbon atoms, by acid catalysis, e.g. with gaseous HCl or concentrated $H_2SO_4$.

$X^-$ is for instance a halogenide, (preferably chloride); sulphate; phosphate; perchlorate: metaperiodate; tetraphenylborate; an alkylsulphonate having from 1 carbon atom (methanesulphonate) to 12 carbon atoms (dodecylsulphonate); trifluoroacetate; tetrahalogenborate; fumarate or alkylsulphate having 10–14 carbon atoms.

Suitable esters 2 include those esters wherein R1 is a straight or branched alkyl group having 1–11 carbon atoms, preferably n-butyl or isobutyl.

The ester 2 is then converted to the acyl derivative 3 wherein OR is a leaving group wherein R is an alkylsulfonyl group having 1–12 carbon atoms, formyl or trifluoroacetyl. Preferably, the alkylsulfonyl group is selected from methanesulfonyl (mesyl), p-toluenesulfonyl (tosyl), p-bromobenzenesulfonyl (brosyl), p-nitrobenzenesulfonyl (nosyl), trifluoromethanesulfonyl (triflyl), nonafluoromethanesulfonyl (nonaflyl) and 2,2,2-trifluoroethanesulfonyl (tresyl). Mesyl is particularly preferred.

The acylation of 2 to 3 is carried out by reacting the ester 2 with $R_2O$, the anhydride of the selected acid wherein R is an acyl group as defined above.

The acylation reaction is carried out in inert anhydrous solvents, such as methylene chloride or acetonitrile or directly in a molten mixture of the two reactants, without any solvent. The acylating agent is added at ratios ranging from 1:1 to 1:5, preferably 1:3, at temperatures comprised between 40° C. and 80° C., for 8–48 hours.

The compound 3 can be isolated (it is not mandatory to isolate the compound 3, as will be shown below), via precipitation with a suitable solvent, such as ethyl ether or hexane. The compound is then purified via crystallization or by eluting its aqueous solution on a weak basic resin such as AMBERLITE IR 45 (Rohm and Haas) or shaking the aqueous solution with a LA-2-type weak basic resin diluted in hexane, and finally lyophilizing or concentrating the aqueous solution.

The ester group $-COOR_1$ of 3 converted to the carboxyl of acyl D-(+)-carnitine 4 via acid hydrolysis with conventional procedures.

Conversion of acyl D-(+)-carnitine 4 to lactone 5 and the conversion of this latter compound to L-(−)-carnitine 6 are carried out as disclosed in the previously cited Italian patent application RM92A000915. This disclosure follows, except that the numbers designating the specific compounds in the Italian patent application have been replaced with the corresponding numbers for the same compounds used herein (e.g., the acyl D-(+)-carnitine is designated "5" in the Italian application and "4" herein; compare SCHEME 1 and SCHEME 2, supra.)

Acyl D-(+)-carnitine 4 is isolated by filtering off the catalyst and then lyophilizing or concentrating the aqueous solution.

Acyl D-(+)-carnitine 4 is then converted to the lactone 5 of L-(−)-carnitine.

The lactonization is carried out in an aqueous basic environment: either with $NaHCO_3$ (ratio 1:1) or with an AMBERLITE IRA-402 basic resin activated in $HCO_3^-$ form or with an LA2 resin. The lactone is isolated by evaporating the aqueous solution or precipitating it as a salt (e.g. as tetraphenylborate or reineckate).

Finally, lactone 5 is converted to L-(−)-carnitine inner salt 6. The lactone is dissolved in water and the resulting solution treated with a base such as $NaHCO_3$ (ratio 1:1), for 8–24 hours.

L-(−)-carnitine is purified from the salts which formed the $X^-$ anion, from the excess—if any—of the acyl halogenide, from pyridine, and the like, by chromatographing the aqueous solution on a strongly acidic resin such as IR 120, eluting with water and then with $NH_4OH$, or—alternatively eluting first on a strongly basic resin such as AMBERLITE IRA 402 activated in $OH^-$ form and thereafter on a weakly acid resin such as AMBERLITE IRC-50.

Preparation of the lactone of L-(−)-carnitine chloride 5b).

$NaHCO_3$ (0.46 g; 5.4 mmoles) was added to a solution of methanesulfonyl D-(+)-carnitine chloride (1.5 g; 5.4 mmoles) in $H_2O$ (25mL) and the resulting solution was kept under stirring for 20 hours. The solution was then lyophilized, the residue taken up with $CH_3CN$ and the undissolved solid filtered off. Following solvent evaporation, 0.98 g, of the title compound were obtained.

Yield: quantitative

TCL=silica gel Eluant=$CHCl_3/MeOH/iPrOH/H_2O/AcOH$ 42/28/7/10.5/10.5

Rf=0.1

$^1$H NMR ($D_2$): δ5.33–5.24 (m, 1H, —CHOCO—); 3.96–3.88 (m, 3H, —$CH_2N^+Me_3$, —C$\underline{H}$HCOO—); 3.53–3.44 (m, 1H, —CH$\underline{H}$COO—); 3.24 (s, 9H, —$N^+Me_3$)

$^{13}$C NMR ($D^2$O): δ6 172.428; 70.671; 68.094; 56.991; 41.394 IR (KBr)=÷($cm^{-1}$) 1850 (C=O)

HPCL

Column=Nucleosil 5-SA; diameter=4 mm; length=200 mm

Eluant=$CH_3CN/KH_2PO_4$ 50 mM (65/35) pH=3.5 with $H_3PO_4$

Flow-rate=0.75ml/min

Retention time=19.23min

Detector=RI Waters 410

Preparation of the lactone of L-(−)-carnitine methanesulfonate (5c).

An aqueous solution of methanesulfonyl D-(+)-carnitine chloride (1.5 g; 5.4 mmoles) was percolated through an IRA-402 resin (30 g) activated to $HCO_3^-$ form and cooled to 5° C., eluting with water at 5° C. till complete elution (controlled by TCL).

The eluate was kept at room temperature for 4hours.

Following evaporation of the aqueous solution, 1.3 g of a raw product which was taken up with $CH_3CN$, were obtained.

Evaporation of the organic solvent yielded 1 g of a white solid.

Yield: 80%.

Differential thermal analysis: incipient decomposition at 160° C. $[\alpha]_D^{25}$+−24.7° (c=1% MeOH) TCL=silica gel Eluant=$CHCl_3/MeOH/iPrOH/H_2O/AcOH$ 42/28 /7/10.5/10.5

Rf=0.1

| Elementary analysis for $C_8H_{17}NO_5S$ | | | |
| --- | --- | --- | --- |
|  | C % | H % | N % |
| Calculated | 40.16 | 7.16 | 5.85 |
| Found | 39.61 | 7.13 | 5.77 |

$_1$H NMR ($D_2$O): δ5.35–5.25 (m, 1H, —CHOCO—); 3.98–3.89 (m, 3H, —$CH_2N^+Me_3$, —C$\underline{H}$COO—); 3.54–3.46 (m, 1H, —CH$\underline{H}$COO—); 3.26(s, 9H, —$N^+Me_3$); 2.81(s, 3H, $CH_3SO_3$—)

$^{13}$C NMR ($D_2$O): δ172.428; 70.671; 68.094; 56.991; 45.320; 41.394

IR (KBr)=v($cm^{-1}$)1835(C=O)

HPCL

Column=Nucleosil 5-SA; diameter=4 mm; length=200 mm

Eluant=$CH_3CN/KH_2PO_4$ 50 mM (65/35)pH=3.5 with $H_3PO_4$

Flow-rate=0.75 ml/min

Retention time=19.48 min

Detector=RI Waters 410

Preparation of L-carnitine inner salt (6) from the lactone of L-(−)-carnitine methanesulfonate (5 c).

$NaHCO_3$ (0.34 g; 4 mmoles) was added to a solution of the lactone of L-(−)-carnitine methanesulfonate (0.96 g; 4 mmoles) in H₂O(20mL) and the resulting solution was kept under stirring at room temperature for 20 hours. The solution was then percolated through AMBERLITE IR-120 resin (20 g) eluting first with water till neutrality to remove methanesulfonic acid and then with 2% NH₃ aqueous solution collecting the eluate till complete elution of L-(−)-carnitine inner salt (controlled by TLC).

Following evaporation of the aqueous solution 0.64 g of L-(−)-carnitine inner salt were obtained.

Alternatively, the reaction mixture was percolated through IRA-402 resin (20 g) activated to OH[31] form, eluting with H₂O till neutrality. The eluate was then percolated through IRC-50 resin (20 g) till complete elution of L-carnitine inner salt (controlled by TLC). Following evaporation of the aqueous solution, 0.64 g of L-(−)-carnitine inner salt were obtained.

Yield: quantitative.

The enantiomeric excess (e.e.) was assessed via the following HPLC method, after L-(−)-carnitine was derivatized with a chiral reagent. As chiral reagent, (+)-1-(9-fluorenyl) ethyl chloroformate (FLEC) was used.

column: Nova-pak $C_{18}(4\mu)$ Cartridge
length: 100 mm
diameter: 5.0 mm
Eluant:
Solution A: 5 mM tetrabutylammonium hydroxide (TBA⁺ OH⁻) and
50 mM $KH_2PO_4$ 75 mL
Acetonitrile 25 ml
brought to pH 7 with 1N KOH
Solution B: Acetonitrile 75 mL
$KH_2PO_4$ 5 mM 25 mL

| | Elution schedule | |
|---|---|---|
| time | % A | % B |
| 0 | 100 | 0 |
| 15 | 100 | 0 |
| 16 | 0 | 100 |
| 22 | 0 | 100 |
| 23 | 100 | 0 |
| 30 | stop | |

Detector=Perkin-Elmer Fluorimeter
Excitation=260 nm
Slit=20 nm
Emission=315 nm
Slit=5 nm L-(−)-carnitine had previously been derivatized with FLEC via the following method; 50 μL of L-(−)-carnitine solution (prepared by dissolving 10 mg carnitine in 50 mL of 50 mM TBA³⁰OH⁻ brought to pH 7 with concentrated H₃PO₄) and 200 μL of solution consisting of 1 mL FLEC in 3 mL acetone, were kept under stirring at 80° C. for 20 minutes.

The solution was cooled and 4 mL of solution A were added thereto. 5 μL of the resulting solution were injected. L-(−)-carnitine $K^1$=5.79 D-(+)-carnitine $K^1$=4.82, absent $$e.e. = \frac{L-D}{L+D} \times 100 = 100\%$$

Preparation of L-carnitine inner salt (6) from methanesulfonyl-D-carnitine chloride (4 b).

NaHCO₃ (0.46 g; 5.4 mmoles) was added to a solution of methanesulfonyl-D-carnitine chloride (1.5 g; 5.4 mmoles) in H₂O (25 mL) and the resulting solution was kept under stirring at room temperature for 20 hours. Further NaHCO₃ (0.46 g; 5.4 mmoles) was then added and the solution was kept under stirring at room temperature for further 20 hours. The title compound was isolated as previously described for the isolation of 6 from 5 b.

L-carnitine is obtained from methanesulfonyl-D-carnitine through the formation of the lactone 5, as evidenced by NMR, HPLC, IR and TLC analysis carried out on a sample obtained by lyophilizing a portion of the solution 20 hours following first NaHCO₃ addition.

It should be understood that, whereas the process disclosed above has been described, for the sake of clarity, as a sequence of five distinct operating steps, the corresponding industrial process consists of three steps only. When the process of the present invention is carried out as an industrial process, the acyl D-(+)-carnitine ester 3 can be directly converted to L-(−)-carnitine inner salt 6 without isolating either the acyl D-(+)-carnitine 4 or the lactone 5.

In fact, the ester of acyl D-(+)-carnitine 3 is hydrolyzed in an acid environment, then the resulting aqueous solution is concentrated and the concentrate is brought to pH 7–9, preferably 8–9 and kept at this pH value for 30–50 hours yielding L-(−)-carnitine.

In the following example which describes one embodiment of the process of the invention, the intermediate compounds 2, 3 and 4 were isolated so as to exhaustively characterize them from a physico-chemical standpoint.

It will be, however, apparent to any expert in organic synthesis that the industrial process comprises the following steps only: (a) conversion of D-(+)-carnitinamide 1 to the ester of D-(+)-carnitine 2; (b) acylating of the hydroxyl group of ester 2 with an anhydride R₂O, wherein R has the previously defined meanings, with the resulting formation of a leaving group OR thus obtaining the ester 3 of acyl D-(+)-carnitine; and (c) conversion of 3 to L-(−)-carnitine inner salt 6.

EXAMPLE 1

Preparation of D-carnitine isobutyl ester chloride 2.
Step (a)

D-carnitinamide chloride 1 (10 g; 0,05 moles) was suspended in 50 mL isobutanol. The solution was cooled to 4° C. and gaseous HCl was added thereto till saturation. The reaction mixture was refluxed for 1 hour and then filtered while still hot, in order to remove NH₄Cl.

The alcohol solution was concentrated to dryness under vacuum, taken up twice with isobutanol and concentrated.

Acetone was added to the residue thus obtained and the solid product filtered off.

11.6 g of compound 2 were obtained.
Yield 90%
HPLC
Column: nucleosil 5-SA 4.0 mm×200 mm
Temperature: 30° C.
Eluant: CH₃CN-KH₂PO₄ 50 mM 65–35 pH 3.5
Flow rate: 0.75 mL/min
Detector I.R.
Retention time: 14.6 min
¹H NMR D₂O δ4.7 (1H,m,C$\underline{H}$OH); 4.0 −3.9 (2H,m, COOCH₂—); 3.5 (2H,m,N$^{+C\underline{H}}$₂—); 3.2 (9H,s,(CH₃)₃N⁺); 2.7 (2H,m,CH₂COO); 2.0 −1.9 (1H,m,C$\underline{H}$(CH₃)₂); 0.9(6H, d,(CH(C$\underline{H}$₃)₂)

| Elemental analysis for $C_{11}H_{24}ClNO_3$ | C % | H % | N % | CL % |
|---|---|---|---|---|
| Calculated | 52.06 | 9.53 | 5.52 | 13.97 |
| Found | 49.89 | 10.26 | 6.23 | 14.88 |

$H_2O$ 0.8% $[\alpha]_D^{25}=+15$ (C=1% $H_2O$)

Preparation of methanesulfonyl D-carnitine isobutyl ester methanesulphonate 3.

Step (b)

A mixture of D-carnitine isobutyl ester chloride (2.5 g; 0.01 moles) and methanesulfonic anhydride (5.2 g; 0.03 moles) was heated at 80° C. for 24 hours.

The molten mass was taken up with $CH_2Cl_2$ and precipitated with ethyl ether. This operation was repeated three times in order to remove the excess of methanesulfonic anhydride.

3.9 g of compound 3 were obtained.

Yield: 100%

HPLC

Column: nucleosil 5-SA 4.0 mm×200 mm

Temperature: 30° C.

Eluant: $CH_3CN$-$KH_2PO_4$ 50 mM 65-35 pH 3.5

Flow rate: 0.75 ml/min

Detector: I.R.

Retention time: 10.11 min $^1$H NMR $D_2O$ δ5.5 (1H,m,-CH-0); 3.9-3.8 (3H,m,$OCH_2$, N+CH-H); 3.6 (1H,d,N+CH-H); 3.2(3H,s,$OSO_2CH_3$);3.1(9H,s,$(CH_3)_3$N+); 3.0 (2H,dd,$CH_2COO$);2.7 (3H,s,$CH_3SO_3$—); 1.8 (1H,m,CH(CH$_3$)$_2$); 0.8 (6H,d,CH(CH$_3$)$_2$).

| Elemental analysis for $C_{13}H_{29}NO_8S_2$ | C % | H % | N % | S % |
|---|---|---|---|---|
| Calculated | 39.88 | 7.47 | 3.58 | 16.38 |
| Found | 39.45 | 7.43 | 3.75 | 16.24 |

$[\alpha]_D^{25}=+24.7$ (c=1% $H_2O$) M.P.=137–140° C.

Preparation of methanesulfonyl D-carnitine methanesulfonate 4.

Step (c)

Methanesulfonyl D-carnitine isobutyl ester methanesulphonate 3 (3.9 g; 0.01 moles) was dissolved in 65 mL 2N HCl and the resulting solution was kept at 50° C. for 20 hours.

The solution was then concentrated to dryness under vacuum. The oily residue was washed with acetone and the solid product which was filtered off.

3.3 g of compound 4 were obtained.

Yield: 90%

HPLC

Column: nucleosil 5-SA 4.0 mm×200 mm

Temperature: 30° C.

Eluant: $CH_3CN$-$KH_2PO_4$ 50 mM 65-35 pH 3.5

Flow rate: 0.75 ml/min

Detector I.R.

Retention time: 12.60 min $^1$H NMR $D_2O$ δ5.5 (1H,m,CHOSO$_2$CH$_3$); 3.9 (1H,dd,N$^+$CH-H): 3.6 (1H,dd,N$^+$CH-H); 3.2 (3H,s,OSO$_2$CH$_3$); 3.1 (9H,s,(CH$_3$)$_3$N+); 2.9 (2H,m,CH$_2$COOH); 2.7 (3H,s, CH$_3$SO$_3^-$)

$[\alpha]_D^{25}=+22$ (C=1% $H_2O$) M.P.=148–150 ° C.

We claim:

1. A process for producing L-(−)-carnitine from D-(+)-carnitinamide, which comprises:

(a) reacting D-(+)-carnitinamide 1 of the formula:

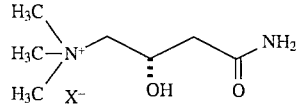

wherein X$^-$ is an anion, in an acid medium with a straight or branched chain aliphatic alcohol, thereby forming ester 2 of the formula:

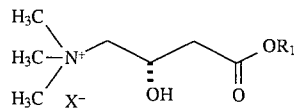

wherein $R_1$ is a straight or branched alkyl group having 1–11 carbon atoms;

(b) acylating ester 2 to an acyl derivative 3 of the formula:

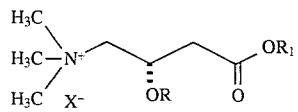

wherein R is an alkylsulfonyl having 1–12 carbon atoms, formyl or trifluoroacetyl group, by reacting ester 2 with an anhydride $R_2O$, wherein R has the above defined meaning;

(c) acid hydrolyzing the $COOR_1$ group of said acyl derivative 3 to a carboxylic acid group, thereby obtaining an acyl D-(+)-carnitine 4 of the formula:

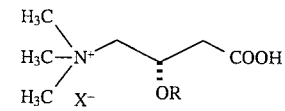

(d) reacting said acyl D-(+)-carnitine 4 with a base thereby preparing lactone 5 of L-(−)-carnitine of the formula:

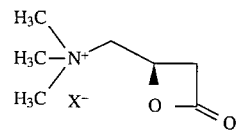

and (e) reacting said lactone 1 with a base and solution thereby forming L-(−)-carnitine and isolating L-(−)-carnitine inner salt by contacting the L-(−)-carnitine containing solution with an ion exchange resin.

2. The process of claim 1, wherein step (b) is conducted in an anhydrous solvent in a ratio of anhydride to reactant ester 2 ranging from 1:1 to 1:5 at a temperature between 40° C. and 80° C. for 8–48 hours.

3. The process of claim 1, wherein step (b) is conducted with a molten mixture of ester 2 and the anhydride in a ratio of anhydride to ester 2 ranging from 1:1 to 1:5 at a temperature of 40° C. to 80° C. for 8–48 hours.

4. The process of claim 1, wherein step (d) is conducted with an aqueous bicarbonate base or with a basic ion exchange resin, and step (e) is achieved by reacting the lactone of step (d) with base in water thereby preparing L-(−)-carnitine.

5. The process of claim 1, wherein:

X$^-$ is halogenide, preferably chloride, sulphate, phosphate, perchlorate, metaperiodate, tetraphenylborate, or alkylsulfonate having 1–12 carbon atoms;

$R_1$ is n-butyl or isobutyl; and

R is methanesulfonyl (mesyl), p-toluenesulfonyl (tosyl), p-bromobenzenesulfonyl (brosyl), p-nitrobenzenesulfonyl (nosyl), trifluoromethanesulfonyl (triflyl), nonafluoromethanesulfonyl (nonaflyl) and 2,2,2-,trifluoroethanesulfonyl (tresyl).

6. A process for producing L-(−)-carnitine from D-(+)-carnitinamide, which comprises:

(a) reacting D-(+)-carnitinamide 1 of the formula:

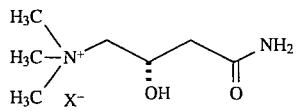

1 wherein $X^-$ is an anion in an acid medium with a straight or branched chain aliphatic alcohol, thereby forming ester 2 of the formula:

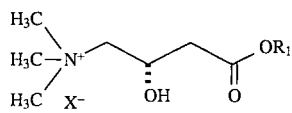

2 wherein $R_1$ is a straight or branched alkyl group having 1 to 11 carbon atoms; and (b) simultaneously acylating ester 2 to prepare an acylated intermediate, hydrolyzing the ester group of the acylated intermediate, reacting the acylated acid intermediate obtained in base thereby forming a lactone intermediate and further reacting the lactone intermediate in base to form L-(−)-carnitine.

* * * * *

UNITED STATES PATENT AND TRADEMARK OFFICE
CERTIFICATE OF CORRECTION

PATENT NO. : 5,532,410
DATED : July 2, 1996
INVENTOR(S) : Fabio GIANNESSI, et al.

It is certified that error appears in the above-indentified patent and that said Letters Patent is hereby corrected as shown below:

On the title page, Items [73] and [22], the Assignee and the Filing Date, should read:

--[73] Assignee: Sigma-Tau Industrie Farmaceutiche Riunite S.p.A., Rome, Italy

[22] Filed: Apr. 7, 1994--

Signed and Sealed this

Eighth Day of October, 1996

Attest:

BRUCE LEHMAN

Attesting Officer     Commissioner of Patents and Trademarks